United States Patent [19]
Switzer, III et al.

[11] Patent Number: 5,192,688
[45] Date of Patent: Mar. 9, 1993

[54] HISTOLOGICAL ANALYSIS METHOD

[76] Inventors: Robert C. Switzer, III, 10053 Thornton Dr., Knoxville, Tenn. 37922; Shannon K. Campbell, Laurel Ave., Knoxville, Tenn. 37919; Tere L. Murdock, 6781 Shoreline Cir., Memphis, Tenn. 38115

[21] Appl. No.: 765,378

[22] Filed: Sep. 25, 1991

Related U.S. Application Data

[63] Continuation of Ser. No. 232,475, Aug. 15, 1988, abandoned.

[51] Int. Cl.$^5$ ............................................. G01N 21/75
[52] U.S. Cl. ........................................ 436/63; 436/86; 436/164
[58] Field of Search ............................. 436/63, 86, 164

[56]      References Cited

U.S. PATENT DOCUMENTS

| | | | |
|---|---|---|---|
| 4,299,917 | 11/1981 | Berger et al. | 435/19 |
| 4,416,998 | 11/1983 | Adams et al. | 436/86 |
| 4,434,234 | 2/1984 | Adams et al. | 436/86 |
| 4,690,901 | 9/1987 | Giammara et al. | 436/86 |
| 4,699,875 | 10/1987 | Appel | 435/4 |
| 4,701,407 | 10/1987 | Appel | 435/4 |
| 4,727,041 | 2/1988 | Arronsakul | 436/8 |
| 4,728,605 | 3/1988 | Fudenberg et al. | 435/29 |

OTHER PUBLICATIONS

Gundersen et al., "Aniline Blue and Silver Nitrate For Staining Developing Insect Nerve Tissue", Stain Technol 51(3), 1976 206-8 (Abstract only).
Williams, "The Telencephalon of the Newborn Dogfish Shark Squalus Aconthias", J. Hirnforsch (W. Germ) 1974, 14/3 (261-285) (Abstract only).
Feigin et al., "Some Chemical Principals Applicable to Some Silver and Gold Staining Methods for Neuropathological Studies", J. Neuro Path. Exp. Neurol, 1976, 63515 (495-507) (Abstract only).
Lieutenant Commander Samuel P. Hicks, A Rapid Pyridine Silver Stain for Nervous Tissue and Reticular Fibers, Medical Corp., United States Navy.
Robert C. Switzer, III et al, A Highly Sensitive Silver Stain for Detecting Proteins and Peptides in Polyacrylamide Gels, Analytical Biochemistry 98, 231–237 (1979).
F. Gallyas, Silver Staining of Micro- and Oligodendroglia by Means of Physical Development, Acta Neuropath. (Berl.) 16, 35–38 (1970).
Lester S. King, The Impregnation of Neurofibrils, Yale Journal of Biology and Medicine.
T. H. James, The Mechanism of Development, The Theory of the Photographic Process, pp. 373–377 (1977).
Robert C. Switzer, III, Neural Argyrophilia Induced by Puromycin: A Directed Golgi-Like Method, Neuroscience Letters, 2 (1976) 301–305.

Primary Examiner—Jill A. Johnston
Assistant Examiner—Lylea Alexander

[57]      ABSTRACT

A method for the controlled histological analysis of brain tissue for the hallmarks of Alzheimer's Disease employing silver staining.

8 Claims, No Drawings

HISTOLOGICAL ANALYSIS METHOD

This is a continuation of application Ser. No. 07/232,475, filed Aug. 15, 1988 now abandoned.

This invention relates to methods for histological analysis of tissue and particularly to the histological analysis of sections of brain tissue for the presence of hallmarks of Alzheimer's Disease.

The hallmark neuropathological features of Alzheimer's Disease (AD) are the neuritic plaques and neurons with neurofibrillary tangles (nfts). Traditionally, these features have been best histologically visualized by one of a number of protocols utilizing silver. Thus, investigations of Alzheimer's Disease have prompted the increased use of histological silver stains. Histological confirmation of the existence of Alzheimer's Disease is not currently practical during the life of the patient. Only after death and subsequent analysis of the patient's brain tissue is confirmation of the existence of the disease possible.

Numerous procedures using silver have been devised for staining sections of brain tissue, but, because of a lack of control in certain steps in many of these methods, there is inconsistent or even a lack of staining of neuritic plaques and nfts. In particular, erratic staining and other problems are common in methods that use a silver-diammine solution (silver nitrate and ammonium hydroxide). Furthermore, the step involving reduction (final development of silver impregnated structures) typically is not easily controlled. For these and other reasons, the prior methods generally are regarded as capricious.

In the analysis of brain tissue for indicators of Alzheimer's Disease, heretofore it has been the practice to look primarily for the presence of the neuritic plaque and nfts. Such hallmarks are still deemed to be good indicators of the existence of the disease. However, in order to obtain information relating to the effects of the disease upon the brain tissue, the general indication of the presence of the plaque and nfts is insufficient. On the other hand, the current histological analysis methods do not provide for the "fine-tuning" necessary to fully detect all nfts and less distinct plaques, nor provide clear differentiation between nondegenerated cells and normal cells, or between specific cell components such as the features of granulovacuolar degeneration (GVD).

A method described by Hicks (J. Lab. Clin. Med 31:1375, 1946 and later modified by others, avoids the use of ammoniacal silver and provides economy and control of treatment. However, the development, or reduction step, is rapid and uncontrollable, being brought about by a solution containing a relatively high concentration of formaldehyde. Other investigators have manipulated variables in silver methods in numerous ways and have distinguished between two means of reduction or development: chemical and physical. Chemical development is the most widely used and is characterized by the transfer of tissue sections from a silver solution to a reducer solution containing formaldehyde. For this step to be successful, it is necessary for there to be a transfer of silver to the reducer solution. The amount transferred is obviously difficult to control. Physical development, on the other hand, brings about the development of micronuclei of silver deposits by growth of the silver deposits from silver provided in the developing solution in controlled amounts and substantially evenly distributed within the developer solution.

Still further, the prior art methods suffer from lack of contrast between the background and the preferentially stained elements of the tissue section. This is particularly true of the common practice of treating the sections after reduction with a gold chloride solution (gold toning) wherein all reds and browns and brownish-blacks are converted into densitites of shades of purplish gray. Due to the rapidity of development by the method of Hicks and others, the tissue section is easily overstained, unevenly stained and the background becomes dark before fainter elements of the section have developed.

In essentially all silver staining methods employed in histological analysis protocols, the section is subjected to the steps of pretreatment (frequently referred to a "sensitization" of the specimen), incubation in a silver solution and reduction of the silver to make it visible. Heretofore, little or no attention has been paid to the incubation stage except to ensure that the section accepts silver. There does not appear to have been a realization that enhancement or suppression of preferential staining is obtainable in the incubation stage.

Accordingly, it is an object of the present invention to provide a new and novel method for the histological analysis of brain tissue. It is another object to provide an improved method for the preparation of brain tissue for visual analysis of the hallmarks of Alzheimer's Disease. It is another object to provide a kit for use in the histological analysis for tissue, especially brain tissue and more especially for analysis for the hallmarks of Alzheimer's Disease.

In accordance with the present invention, the tissue in question normally exists as freeze-cut or paraffin-impregnated sections prepared by methods well-known in the art. Paraffin sections commonly are on the order of 7 microns thick whereas freeze-cut sections range upwardly to 40–50 microns thick. A freeze-cut section may be prepared for staining by removing from the section extraneous materials that might interfere with staining and development. Paraffin-cut sections may be prepared by dissolving the paraffin in xylene and then rehydrating with water. Thereafter, in the present method either type of the section is incubated in a pyridine-silver-carbonate staining solution, followed by a citric acid wash and an acetic acid bath. The incubated section is thereafter subjected to a physical developer comprising a combination of solutions of (a) sodium carbonate, (b) ammonium nitrate, silver nitrate, and tungstosilicic acid, and (c) solution (b) plus formaldehyde.

More specifically, a brain from autopsy is fixed in 10% phosphate buffered (pH 7.4) formaldehyde by immersion and, where possible, the brain is perfused through the circle of Willis. After at least a week in formaldehyde, thick slabs from the brain tissue are immersed overnight in a cryoprotecting solution of 10% ethanol in a 10% formaldehyde solution in preparation for freeze-sectioning at 40 microns. Preferably sections are collected into a 4×6 array of freezable containers (e.g. specimen cups) containing a 10% solution of formaldehyde.

The solutions employed in a preferred embodiment of the present method are prepared as follows:

| Solution: | |
|---|---|
| I. 2% Ammonia Water: | |
| Ammonium Hydroxide (29.5% NH$_3$) | 2 ml |
| Distilled Water - make just before use | 100 ml |
| II. 1% Silver Nitrate: | |
| Silver Nitrate (AgNO$_3$) | 0.6 gm |
| Distilled Water | |
| III. 1% Potassium Carbonate: | |
| Potassium Carbonate (K$_2$CO$_3$) Anhydrous | 0.5 gm |
| Distilled Water | 50 ml |
| Note: The K$_2$CO$_3$ MUST be reagent grade and anhydrous; | |
| IV. Pyridine-Silver-Carbonate Staining Solution: | |
| 1% AgNO$_3$ | 60 ml |
| Pyridine (preferably reagent grade) | 3 ml |
| Note: Do not use plastic, disposable pipettes to dispense the pyridine. | |
| 1% K$_2$CO$_3$ | 45 ml |
| Note: Add the pyridine to the silver nitrate solution and stir; then add the potassium carbonate to the silver-pyridine mixture and stir well. It is important to add the solutions together in the order listed so that no precipitate will form. | |
| V. 1% Citric Acid: | |
| Citric acid monohydrate | 1 gm |
| Distilled Water | 100 ml |
| Note: This solution should not be more than 3–5 days old. | |
| VI. 0.5% Acetic Acid: | |
| Acetic Acid, Glacial | 1 ml |
| Distilled Water | 100 ml |
| VI. Physical Developer: | |
| Solution A: | |
| Sodium carbonate | 25 gm |
| Distilled Water | 500 ml |
| Solution B: | |
| Ammonium Nitrate | 1 gm |
| Silver Nitrate | 1 gm |
| Tungstosilicic Acid (fw 2874) | 5 gm |
| Distilled Water | 500 ml |
| Note: These ingredients are to be dissolved in the order in which they are listed. | |
| Solution C: | |
| Prepare exactly as Solution B and then add 3.5 ml of 37% formaldehyde (Commercial strength) | |
| The Physical Developer is prepared by mixing the following amounts of Solutions A, B & C, in the order given, with vigorous stirring: | |

| Freeze-Cut Sections | Paraffin Sections |
|---|---|
| Sol'n. A - 50 ml | Sol'n. A - 50 ml |
| Sol'n. B - 45 ml | Sol'n. B - 40 ml |
| Sol'n. C - 5 ml | Sol'n. C - 10 ml |

| | |
|---|---|
| Note: If the resultant solution is anything but clear, discard and remix, slowly adding B, then C. | |
| VIII. Mounting Solution for Freeze-cut Sections | |
| Stock Acetate Buffer, pH 4.6: | |
| 0.2 M Sodium acetate | 500 ml |
| 0.2 M Acetic Acid | 500 ml |
| Acetate Buffer Mounting Solution: | |
| Stock Acetate Buffer | 24 ml |
| Distilled Water | 1000 ml |
| Triton X | 4 drops |

Various substitutions in these solutions will be obvious to one skilled in the art. For example, potassium, lithium or sodium carbonate may be employed as the source of carbonate in Solution IV; in Solution A of Solution VI, lithium carbonate or sodium carbonate, but not potassium carbonate may be employed; a reducing agent equivalent to formaldehyde may be employed; a chelating agent equivalent to citric acid may be employed; a suitable weak acid equivalent to acetic acid may be employed, etc. Further, the concentrations given are preferred and obviously may be varied by small amounts without destroying the ability to obtain staining, but such variations often will produce less than optimum results, except however, as noted hereinafter, variation of the concentration of pyridine in Solution IV has pronounced, and at times desirable, effects. In like manner, it is not desirable to increase the concentration of formaldehyde in the physical developer (Solution VI) beyond about 0.2% by volume and preferably such concentration is about 0.013% for processing freeze-cut sections. For processing paraffin sections, the preferred percentage is by approximately 0.026%.

In the preferred embodiment, the pH of the incubation solution (Solution IV) between about 10.5 and 11.5 depending upon the concentration of pyridine as is described hereinafter. The pH of the physical developer (Solution VI) is about 10.5.

In a typical staining sequence, sections freeze-cut at 25–40 microns are collected and stored in 10% formaldehyde and then taken through the sequence set forth below. All steps in this sequence are conducted at approximately room temperature. To transfer free-floating sections between most steps, a basket can be used consisting of a short glass cylinder with a synthetic fiber fabric stretched across one end and secured with silicon sealant/adhesive. It has been found best, however, to use an L-shaped glass rod, suitably tapered, to transfer sections into and out of the silver-pyridine-carbonate (Solution IV) and the physical developer (Solution VII). Crystallizing dishes are preferred for containing the sections during the incubation and development steps. Basket transfer can be safely used for all other steps.

Step 1. Rinse twice in distilled or deionized water to remove excess formalin, 5 minutes per rinse. For paraffin sections, dewax in xylene and rehydrate to water.

Step 2. Place sections to be stained (4–8 sections at a time) in ammonia water (Solution I) for 5 minutes, agitating gently.

Step 3. Rinse sections in two changes of distilled water—1 minute each.

Step 4. Place the sections into the pyridine-silver-carbonate solution (Solution IV) for 40 minutes.

Step 5. Immerse sections in 1% citric acid for 3 minutes.

Step 6. Immerse sections in 0.5 % acetic acid for 3 minutes minimum.

Step 7. Place the sections in the physical developer solution for 90 seconds to 3 minutes. Monitor the progress of development with a dissecting microscope provided with illumination from below. A microscope on a stand with an extension arm that can be moved over the sections on a light box is most satisfactory. One section at a time is removed from the acetic acid of Step 6 and developed individually to obtain the optimum development of the components of the section.

Step 8. The developed section is placed in 0.5% acetic acid for 2 minutes. This stops the development.

Step 9. The sections are water rinsed and mounted out of acetate buffer-Triton X mounting solution (Solution VIII).

Step 10. The mounted sections are dehyrated (air dried), cleared in xylene, and coverslipped.

In paraffin sections stained in accordance with the present invention the neurofibrillary tangles are distinctly black to brown black while other parts of the neuron cell body, if still intact, are rust or amber. The neurite components of the plaque typically stain black or brownish black but depending on the type of plaque there can be fewer or greater numbers of black neurite profiles among the other components of the plaque that are amber colored. In the background some single neurites can be seen to be stained. With further time in the physical developer, the number of such neurites increase in frequency until the background takes on the appearance of an almost solid color so that the contrast between plaques, especially small ones, and the background is diminished and makes detection of the plaques more difficult.

In paraffin sections, the features of granulovacuolar degeneration (GVD) are visible as individual, amber granules, more or less concentric within a clear, unstained sphere within the colored cytoplasm. This is contrasted with the prior methods wherein the expected surrounding unstained sphere is not detectable and the granules appear more coarse and are intermingled with other spheres and smaller silver-stained granules, thereby making it difficult to be certain that one is observing true GVD features. Lipofuscin granules stain distinctly black with the present method whereas these granules exhibit little or no staining in the prior methods.

In either paraffin or freeze-cut section Myelin staining typically is faint with the present method, thereby preventing the obstruction of features in the deeper layers of cortex and in the white matter where, in some cases, neuritic plaques have been found by the present inventors. Such deep-lying plaques have heretofore gone unnoticed in many instances due to the inability of the prior methods to permit the differential staining which the present methods provides and which is required if one is to observe the deeper layers.

In the present method, the freeze-cut, 40 micron sections will have a light amber or yellow appearance by the time they reach the physical developer (Step 7). Examination with a dissecting microscope may reveal some neuritic plaques, even at this stage. Shortly after immersing a section in the physical developer, neuritic plaques begin to be prominent. Although full staining of the plaques is usually accomplished in 1-2 minutes, the end point should be determined for each section with the aid of a dissecting microscope. Insufficient development yields pale profiles of plaques and neuron cell bodies with neurofibrillary tangles. Over-development results in a dark amber background, intensified staining of the glia and myelin, and staining of normal fibers of the neuropil. It has been found valuable to develop some sections for times that are slightly less and slightly more than what appears to be the time for optimal staining for the majority of cases. For example, if 1.5 minutes yields optimal staining, it is preferred to develop 1 or 2 sections for 1 minute and 1 or 2 sections for 2 minutes. This bracketing of development times can be very useful since plaques in different areas of the brain appear to develop at different rates. While plaques in the amygdala may be fully developed in a given time period, the plaques in the adjacent areas of cortex and striatum and, especially, very small plaques are only revealed with further development. Other than the adjustment of the time of residence of the section in the physical developer, the other times referred to in Steps 1-6 and 8 are to be deemed illustrative of preferred times and not limiting of the invention. For example the 40 minutes incubation time at room temperature can be reduced to less than about 2 minutes by placing the incubating sections in a microwave oven.

The most difficult aspect of control in any prior art staining procedure lies in the reduction step where minute silver deposits are converted to visible objects. In the present method the use a physical developer brings about the development of micronuclei of silver deposits in a controlled fashion. Contrary to the prior methods, in the present physical developer there is provided a reducing agent, formaldehyde, in low concentration. It is felt that this lower concentration slows down the reduction process, giving more control over the process. In addition, the silver in the physical developer appears to provide uniform availability of silver ions at the micronuclei sites so that all cell components which have been "incubated" have the opportunity to, and do, grow and develop into visible images.

In the present method, the inventors have discovered that control of the developing stage is possible in substantial part by selection of and control over the incubation stage. More specifically, in the present method the degree of "sensitization" of the sections in the incubation stage appear to be a function of the development of the number and apparently the size of the micronuclei sites created in the cell components in the section. Through the choice of concentration of pyridine in the incubation solution (Solution IV), it appears that more or less micronuclei sites are created. In turn, and in combination with the physical developer having a low concentration of formaldehyde (reducing agent) and free silver in solution and readily available to the micronuclei sites for their growth during the development stage, these micronuclei develop (grow) and exhibit the characteristic colors and clarity noted herein.

Thus, the concentration of pyridine in the incubation solution (Solution IV) is of substantial importance in the present method. The results of varying the concentration of pyridine in Solution IV of the preferred method described herein is presented in Table 1.

Concentrations of pyridine below about 2.5% (3 ml) in the incubation solution do not provide effective differentiation of sensitization between cell components of the nervous tissue. On the other hand, concentrations of pyridine greater than about 12% (14 ml) appear to "hypersensitize" the section so that there is intense development of a single or small number of cell components.

The presence of tungstosilicic acid provides a colloid protectorant which prevents spurious reduction of silver except on preestablished silver nucleation sites.

TABLE 1

| NEURAL ELEMENTS | PYRIDINE VARIATIONS | | | |
|---|---|---|---|---|
| | 3 ml | 8 ml | 11 ml | 14 ml |
| RED BLOOD CELLS | %-3 | %-2 | %-2 | %-1 |
| | I-3 | I-2-1 | I-2-1 | I-2-1 |
| | C-Black | C-Brown | C-Pale Brown | C-Pale Brown |
| GLIA | %-3 | %-3 | %-2 | %-2 |
| | I-3 | I-2 | I-1-0 | I-1-0 |
| | C-Black | C-Brown | C-Pale Brown | C-Pale Brown |

TABLE 1-continued

| NEURAL ELEMENTS | PYRIDINE VARIATIONS | | | |
|---|---|---|---|---|
| | 3 ml | 8 ml | 11 ml | 14 ml |
| NORMAL NEURONS | %-3 | %-2 | %-1-0 | %-0 |
| | I-2 | I-2-1 | I-1-0 | I-0 |
| | C-Amber Rust | C-Amber | C-Pale Orange None | C-None |
| TANGLED NEURONS | %-3 | %-3-2 | %-2-1 | %-2-1 |
| | I-3-2 | I-3-2 | I-2-1 | I-2-1 |
| | C-Black-Brown | C-Black-Brown | C-Dark Brown (Amber) Orange | C-Brown-(Amber) Orange |
| NEURITIC PLAQUES | %-2 | %-2 | %-3 | %-3 |
| | I-2 | I-2-3 | I-3 | I-3 |
| | C-Brown | C-Dark Brown-Black | C-Black | C-Black |

% - Number of Elements Staining
3 - High
2 - Med.
1 - Low
0 - None
I - Intensity of Staining Affinity for Silver
3 - High
2 - Med.
1 - Low
0 - None
C - Ideal Color Range Further control of development is accomplished by varying the time in developer and by adjusting the ratio of the amounts of the developer and of Solutions B and C of Solution VI. It will be recalled that Solution C contains the reducing agent, i.e. formaldehyde, and therefore the quantity of Solution C in the physical developer adjusts the absolute amount of formaldehyde present in the physical developer. By adjusting the ratio of Solutions B & C, the degree and kind of micronuclei growth can be selected. If more of Solution C is used to accelerate development, then the amount of Solution B that is used is reduced by a corresponding amount so the sum of the quantities of Solutions B & C always equals 50 ml (always results in the same ratio of Solution A to the combination of Solutions B & C).

Physical development of the sections is halted by immersion of the sections in acetic acid which serves to change the required alkaline pH of the physical developer solution to an acid pH. Contrary to prior methods, in the present method, the sections may be removed from the acetic acid solution and returned the the physical developer to restart the development process if desired. This starting and stopping of the physical development may be repeated as many times as desired. For example, the development process may be stopped to allow the observation of particular visible features of certain cell components and thereafter returned to the developer solution to develop other of the cell components whose development may obscure the first-observed cell components. Thus contrary to the prior methods, the degree of staining can be adjusted to suit the analyst's preference or to meet other criteria, such as resolving components of a neuritic plaque as noted above, or obtaining high contrast between plaques and background for video image analyses.

Notably, the present method consumes less silver than the prior methods, thereby reducing the overall costs of the procedure. Further, the present method eliminates the use of ammonical silver which, even with careful preparation, commonly yields variable results. Gold toning as used in certain prior methods is eliminated in the present method since this practice tends to stain more of the background neuropil than is preferred in obtaining optimal differentiation of the cell components sought to be observed.

The sensitivity of the present method to contamination or to slight inconsistencies in technique is minimized by using all glassware for any containers, transfer devices, stirrers, etc. and first rinsing the same with concentrated nitric acid and then with deionized water prior to use.

In accordance with one aspect of the present invention, there is provided a merchantable kit for use in the histological analysis of brain tissue for the hallmarks of Alzheimer's Disease. A merchantable kit for use in analyzing a batch of freeze-cut sections of 10-15 slides per batch employing the preferred method of the present invention, includes the following:

| 1. Pre-Wash Solution | |
|---|---|
| 2% ammonium hydroxide | 50 ml |
| 2. Staining Solution | |
| Part A: 1% silver nitrate | 15 ml |
| Part B: 1% potassium carbonate | 25 ml |
| Part C: pyridine | 10 ml |
| 3. Post Stain Wash | |
| citric acid | 1 gm |
| 4. Pre-development Wash | |
| 0.5% acetic acid | 50 ml |
| 5. Physical Developer | |
| Part A: | |
| 5% sodium carbonate | 25 ml |
| Part B: | |
| 0.2% ammonium nitrate | 25 ml |
| 0.2% silver nitrate | |
| 1.0% tunstosilicic acid (fw 2874) | |
| 0.013% formaldehyde | |
| 6. Post-Development Stop | |
| 0.5% acetic acid, glacial | 50 ml |

For processing paraffin sections, the kit includes the same ingredients as above except that Part B of the physical developer is changed to includes:

| 0.2% ammonium nitrate | 25 ml |
|---|---|
| 0.2% silver nitrate | |
| 1.0% tungstosilicic acid | |
| 0.026% formaldehyde | |

As noted herein, silver staining of cell components by the prior art methods is deemed capricious. By means of the present kit, the inventors supply prepared solutions in which the desired chemicals have been premixed, in the proper amounts and in the proper order of mixing, under controlled conditions. Such premixed solutions save considerable time of a laboratory technician when performing an histological analysis of brain tissue for AD. Most importantly, however, the availability of premixed solutions provides for improved accuracy of the analysis by removing the possibility of technician error in preparation of the solutions. Further, duplicate analysis using premixed solutions results in improved reproducibility of results which can be of great importance in formulating a final opinion as to what the analysis shows regarding AD.

What is claimed is:

1. A method for the histological analysis of tissue for the hallmarks of Alzheimer's Disease comprising the steps of:
    selecting a section of nerve tissue,
    incubating said section in a first solution of pyridine, silver and carbonate for a period of time sufficient to cause said solution to substantially permeate said section and generate multiple silver micronuclei sites within selected ones of the cell components of said tissue,
    said pyridine being present in said first solution at a concentration of between about 2.5% and 12% by volume, developing said section in a physical developer solution comprising (a) silver ions, alkali metal carbonate, ammonium nitrate, Tungstosilicic acid, and formaldehyde as a reducing agent, for time sufficient to produce silver deposits at micronuclei sites generated during incubation of said section,
    said quantity of reducing agent being effective for providing control over the development of the micronuclei sites,
    thereafter subjecting said section to a dilute acid solution for a time sufficient to reduce the pH of the environment of the section to below about 7 and halt further reduction of silver within said section, and
    analyzing said section of nerve tissue for the presence of the hallmarks of Alzheimer's Disease, including neuritic plaques and neurons with neurofibrillary tangles.

2. The method of claim 1 wherein said formaldehyde is present in a concentration less than about 0.2% by volume.

3. The method of claim 1 wherein said alkali metal carbonate is selected from the group consisting of sodium carbonate, potassium carbonate and lithium carbonate.

4. The method of claim 1 wherein said nerve tissue is selected from a human brain.

5. A method for the histological analysis of human brain tissue for the hallmarks of Alzheimer's Disease comprising the steps of:
    selecting a section of said brain tissue,
    eliminating from said section substantially all foreign material other than water,
    thereafter subjecting said section to an incubation solution comprising silver ions and alkali metal carbonate ions in the presence of sufficient pyridine to develop a multiplicity of silver micronuclei sites within individual ones of the cells components of said tissue section,
    removing said section from said incubation solution when a sufficient accumulation of silver is provided at said micronuclei sites for the generation thereof,
    thereafter subjecting said section to a physical developer solution containing silver ions, carbonate ions, ammonium nitrate, Tungstosilicic acid, and formaldehyde as a reducing agent at a concentration sufficiently low as permits the visible observation of the development process,
    halting said development process when visual observation of the section indicates that sufficient silver has deposited at said micronuclei sites to provide clear differentiation of individual ones of the cell components of said tissue, and
    analyzing said human brain tissue for the presence of the hallmarks of Alzheimer's Disease, including neuritic plaques and neurons with neurofibrillary tangles.

6. The method of claim 5 wherein said pyridine is present in a concentration of between about 2.5% and 12% by volume.

7. The method of claim 5 wherein said reducing agent is present in a concentration of between about 0.010% and 0.2% by volume.

8. The method of claim 5 wherein said carbonate ions in said developer solution are selected from the group consisting of sodium, and lithium carbonates.

* * * * *